United States Patent [19]

Braquet

[11] Patent Number: 4,897,421

[45] Date of Patent: Jan. 30, 1990

[54] OPHTHALMOLOGICAL COMPOSITION OF MATTER AND A METHOD FOR TREATMENT OF OCULAR INFLAMMATION BY SAID COMPOSITION

[75] Inventor: Pierre Braquet, Garches, France

[73] Assignee: Societe De Conseils de Recherches et D'Application (S.C.R.A.S.), France

[21] Appl. No.: 190,761

[22] Filed: May 6, 1988

[30] Foreign Application Priority Data

May 7, 1987 [GB] United Kingdom ............... 8710780

[51] Int. Cl.[4] .............................................. A61K 31/19
[52] U.S. Cl. ..................................... 514/557; 514/914
[58] Field of Search ............................... 514/557, 914

[56] References Cited

U.S. PATENT DOCUMENTS 4,599,353 8/1986 Bito ..................................... 514/573
4,616,012 10/1988 Neustadt et al. ................. 514/223.2

Primary Examiner—Stanley J. Friedman
Assistant Examiner—Zohreh A. Fay
Attorney, Agent, or Firm—Lucas & Just

[57] ABSTRACT

The present invention relates to an ophthalmological composition of matter comprising a suspension of eicosapentaenoic acid in an alkyl cellulose and/or hydroxyalkyl aqueous cellulose solution to be used in any case of ocular inflammation on men and/or on animals.

The invention also relates to the use of said eicosapentaenoic acid and to a method for the treatment of ocular inflammation by the same.

8 Claims, No Drawings

OPHTHALMOLOGICAL COMPOSITION OF MATTER AND A METHOD FOR TREATMENT OF OCULAR INFLAMMATION BY SAID COMPOSITION

DESCRIPTION:

The present invention relates to a new ophthalmological composition, the active ingredient of which is eicosapentaenoic acid.

Eicosapentaenoic acid, abbreviated hereafter as "EPA", means cis-5, 8, 11, 14, 17-eicosapentaenoic acid of the formula

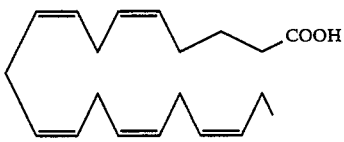

EPA is a known polyunsaturated fatty acid from the marine food chain, serving as a precursor for the prostaglandin-3 and thromboxane-3 families. It differs from arachidonic acid by the inclusion of an extra double bond between the 17- and 18-C atoms.

The invention provides an ophthalmological composition comprising a suspension of EPA in an alkyl cellulose and/or hydroxyalkyl cellulose aqueous solution. The EPA is preferably present in an amount of from 0.5 to 3 %, more preferably 1 %. Methyl cellulose and hydroxypropyl cellulose are the preferred alkyl cellulose and hydroxyalkyl cellulose respectively, and the cellulose solution is preferably a 0.5 % solution.

The invention also provides eicosapentaenoic acid for use as a medicament for topical application to the eye.

The invention further provides use of eicosapentaenoic acid for the manufacture of a medicament for topical application to the eye.

Finally, the invention provides a method for the treatment of ocular inflammation, the method comprising topically administering eicosapentaenoic acid to the eye.

The interest of this ophthalmological composition according to the present invention is illustrated by the following experimentation carried out using eicosapentaenoic acid containing ophthalmological compositions on rabbit eyes.

EXPERIMENTATION

This experimentation was conducted on male pigmented chinchilla rabbits weighting 2.0-2.5 kg. All eyes were initially examined with a slit lamp. Only animals without any sign of ocular inflammation were included in the study. Immunization of the pigmented rabbits was performed by injection of 20 $\mu$l pyrogen free human serum albumin (HSA, 20 % solution) into the cornea of both eyes, according to Morawiecki method, after corneal anaesthesia with 0.4 % oxybuprocaine and sedation by Hypnorm® (fluanison 10 mg/ml and phentanyl citrate 0.2 mg/kg body weight).

The results were appreciated by measuring corneal oedema formation and by determining the fatty acids in corneal tissues.

(a) Measuring corneal oedema formation

Rabbit eyes were treated with fatty acid suspensions prepared with 0.5 % hydroxypropyl cellulose as vehicle. These suspensions were prepared immediately before application. Controls were treated with the vehicle only. Treatment with the fatty acid preparations, one eyedrop of 30 $\mu$l three times a day instilled into the conjunctival sac was started eight days after immunization ad continued for the duration of the experiments. Keratitis of the rabbit eye was evaluated by measuring corneal oedema formation, neovascularization and the occurance of the annular leukocyte infiltrate in the cornea (Wesseley's ring). These three parameters of corneal inflammation can be well observed in vivo. The clinical observation was organized in a double masked fashion and for each animal the values of both eyes were averaged. The corneal aspect was appreciated by counting the number of days during which opaque rings or a diffuse completely opaque cornea were visible as well as the number of days on which vessels into the cornea were visible.

A Haag-Streit slit lamp with a pachymeter fitted with central fixation lights according to Mishima and Hedbys was used for these measurements. From each eye, the mean of three measurements was taken.

Central corneal thickness was measured before and at the 7, 9, 11, 14, 16, 18, 20, 23 and 27th day after intrastromal injection with HSA. For each animal the differences between the pachymetry measurements before and after intraocular injection with HSA were regarded as oedema ($= \Delta$corneal thickness).

(b) Determination of fatty acids in lipids of corneal tissue after topical treatment with eicosapentaenoic acid or columbinic acid Three groups of four rabbits with uninflamed eyes received three times daily during four days a 30 $\mu$l eye drop of either the vehicle (0.5 % hydroxypropyl-methyl cellulose in water) or a suspension of 3% columbinic acid or 1% eicosapentaenoic acid in the vehicle. Rabbits were sacrificed using an overdose of penthothal on the fifth day four hours after they received a last dose of topically applied eicosapentaenoic acid or columbinic acid. Using a 14 mm trephane the corneas were dissected from the intact enucleated eye. The corneas were washed four times in saline to prevent contamination in the analytical procedure with topically applied fatty acids. In each of the three groups of animals right and left eyes were pooled separately for fatty acid analysis.

One volume of methanol was added to the pooled samples and they were stored at $-60°$ C. till biochemical analysis. Lipids were extracted from the corneal tissues with a mixture of chloroform : methanol (2:1).

The chloroform layer was concentrated with a stream of nitrogen and the residue was transesterified with methanolic hydrochloric acid (2h, 65° C).

After extraction with a mixture of hexane/diethyl ether 50/50 and evaporation of the solvent with a stream of nitrogen, the fatty acid esters were chromatographed over silica columns with hexane/diethyl ether 90/10. The fatty acid methyl esters were analyzed with gas liquid chromatography after removal of the solvent with a stream of nitrogen. A HP 5880 Gas chromatograph equipped with an automatic sampler (7672 A, Hewlett-Packard) and a FID detector employing a WCOT glass capillary column (CP SIL 88, 1=25 cm, i.d. 0.22) were used ; injection temperature 225° C., detection at 350.C, programmed from 110° C. to 186° C. with 2° C./min. and 10 min. hold at the final temperature.

Statistical analysis

Data were analyzed by non parametric methods to avoid assumptions about the distribution of the variables involved. Wilcoxon's signed-rank test was applied for the mean pachymetry data obtained at several time points in the treated and untreated groups during the period of inflammation and the Mann-Whitney U-test served for analysis of the duration of neovascularization and corneal opacification in the treated and untreated eyes at any given time. Significance of difference is given for two tailed observations, P values <0.05 were regarded as significant.

Topical application of arachidonic acid neither increased nor decreased the inflammatory response (table I).

TABLE I

CORNEAL OPACITY, GROWTH OF VESSELS AND OEDEMA FORMATION DURING IMMUNOGENIC KERATITIS

|  | Duration of corneal opacity (days)° | Duration of corneal neovascularization (days)° | Pachymetry AUC (% compared to controls)° |
|---|---|---|---|
| Controls (n = 16) | 6,7 ± 0,5 | 7,2 ± 0,8 | 100 ± 13 |
| Columbinic acid 3% (18:2 n-6 trans) (n = 8) | 3,7 ± 0,7*** | 3,7 ± 0,7** | 47 ± 10++ |
| Eicosapentaenoic acid 1% (20:5 n-6) (n = 8) | 3,3 ± 0,5*** | 4,3 ± 0,8* | 60 ± 11++ |
| Dihomo-γ-linolenic acid 1% (20:3 n-6) (n = 8) | 3,9 ± 0,5** | 4,9 ± 0,9 | 70 ± 15+ |
| γ-linolenic acid 1% (18:3 n-6) (n = 8) | 4,6 ± 0,5* | 4,8 ± 0,6** | 71 ± 12++ |
| Arachidonic acid 1% (20:4 n-6) (n = 8) | 5,3 ± 1,0 | 6,4 ± 1,0 | 97 ± 21 |

AUC: : Area under the curve
°: mean ± SEM
Significance of difference vs controls for duration of corneal opacity and vessel growth was calculated with the Mann-Whitney U test.
*$p < 0,05$
**$p < 0,01$
***$p < 0,002$
+$p < 0,05$
++$p < 0,01$
Mean pachymetry values of controls and treated animals at various points during the inflammation were tested for significance with Wilcoxon's signed rank test.

RESULTS

Non-treated eyes

The appearance of keratitis in vehicle treated eyes was as follows. One week to ten days after intracorneal injection of HSA, clouding of the cornea started at the limbus and on about day 14–17 a white ring of opacification known as Wesseley's ring appeared.

The ring occurred for one to eight days. Within an interval of two to four days vascularization of the cornea started from the limbus, progressed till about day 22–25 and then regressed quickly resulting in all cases in a clear cornea 30 days after the injection of the HSA.

All animals injected with HSA responded with white ring formation and neovascularization. Corneal oedema formation recorded with pachymetry started around day seven and lasted till day 30.

Eyes treated by fatty acids

In rabbits treated with EPA, columbinic acid, DHGL and γ-linolenic acid, the period of corneal opacification was significantly shorter in comparison with the controls. Vessel growth was significantly diminished after treatment with EPA, columbinic acid and γ-linolenic acid (table I). These substances and DHGL also significantly inhibited corneal oedema formation.

Fatty acids in lipids of corneal tissue after topical treatment with eicosapentaenoic acid or columbinic acid After four days of topical treatment, EPA treated animals showed the occurence of 1,8 % EPA (20:5 n-3) and 2.5 % of its metabolite 22:5 n-3 in the corneal phospholipids (see table II).

Columbinic acid treated animals showed the occurence of 5,6 % of this fatty acid in the corneal phospholipids.

After treatment with both EPA and columbinic acid, arachidonic acid (20:4 n-6) level decreased and further metabolization of arachidonic acid to 22:4 n-6 was partially inhibited 1.9 % respectively 2.5 % 22:4 n-6 in treated animals compared to 3 % in controls. Also the oleic acid (18:1) level decreased and the palmitic acid (16:0) level increased in the corneal phospholipids of EPA and columbinic acid treated animals. The total amount of the free fatty acids was 4 % of the amount of phospholipid bound fatty acids. Columbinic acid and EPA occurred in the free fatty acid fraction, however the level of these fatty acids was small compared to the phospholipid bound fraction.

DISCUSSION

The fatty acids columbinic acid, eicosapentaenoic acid and γ-linolenic acid were effective in the inhibition of leukocyte infiltration, neovascularization and corneal oedema formation. Regarding neovascularization and corneal oedema, columbinic acid showed the most effective inhibition. Eicosapentaenoic acid was the most effective inhibitor of leukocyte infiltration. DHGL acid showed a significant inhibition of leukocyte infiltration and oedema formation but not of neovascularization. Arachidonic acid treatment had neither an inhibitory nor a stimulating effect on the paramaters of the immune-complex keratitis.

TABLE II

THE EFFECT OF TOPICAL ADMINISTRATION OF COLUMBINIC ACID (18:3 5,9,12) OR EICOSAPENTAENOIC ACID (20:5 n-3) ON THE COMPOSITION OF RABBIT CORNEAL TISSUE PHOSPHOLIPID BOUND AND FREE FATTY ACIDS

| Fatty acid | | Fatty acid composition (weight) | | | | | |
|---|---|---|---|---|---|---|---|
| | | Controls | | Columbinic acid | | Eicosapentaenoic acid | |
| Numerical symbol | Trivial name of fatty acid | PL | FFA | PL | FFA | PL | FFA |
| 16:0 | palmitic | 10.9 | 0.7 | 13.8 | 0.4 | 15.8 | 0.7 |
| 18:0 | stearic | 8.9 | 1.4 | 10.6 | 0.9 | 9.0 | 1.1 |
| 18:1 n-9 | oleic | 42.5 | 0.8 | 37.1 | 1.4 | 35.7 | 1.1 |
| 18:2 n-6 | linoleic | 0.9 | 0.0 | 0.7 | 0.1 | 0.5 | 0.0 |
| 18:3 5,9,12 | columbinic | 0.0 | 0.0 | 5.6 | 0.4 | 0.0 | 0.0 |
| 20:4 n-6 | arachidonic | 7.5 | 0.0 | 5.9 | 0.2 | 4.9 | 0.0 |
| 20:5 n-3 | eicosapentaenoic | 0.0 | 0.0 | 0.0 | 0.0 | 1.8 | 0.1 |
| 22:4 n-6 | | 3.0 | 0.0 | 2.5 | 0.1 | 1.9 | 0.0 |
| 22:5 n-3 | | 0.7 | 0.0 | 0.5 | 0.0 | 2.5 | 0.1 |
| 22:6 n-3 | docosahexanoic | 0.3 | 0.0 | 0.0 | 0.0 | 0.3 | 0.0 |

Values are the mean of two pooled corneal tissue preparations obtained from four different animals, extracted and analyzed as described in the methods section. The numbers are the percentages of total fatty acids. The numerical symbol designates the chain length and the number of double bounds of fatty acid, n designates the place of the first double bound. (PL = phospholipid bound, FFA = free fatty acids).

Animals treated only with vehicle responded for 100% with corneal opacification, neovascularization and oedema. The appearance of opaque rings and neovascularization in the cornea is in accordance with previous observations using this model of corneal anaphylaxis.

PRESENTATION - POSOLOGY

Preferred presentation comprises a 0.5 to 1 % in weight of EPA in a methyl cellulose/hydroxypropyl aqueous suspension. Usual posology is three instillations per diem for about 10 days.

INDICATION

The composition according to the invention is to be used in any case of ocular inflammation on men and/or on animals.

I claim:

1. An ophthalmological composition comprising an ophthalmologically effective amount of eicosapentaenoic acid in a pharmaceutically acceptable carrier.

2. An ophthalmological composition according to claim 1 in which the eicosapentaenoic acid is present in an amount of from 0.5 to 3%.

3. An ophthalmological composition according to claim 1 or claim 2 in which the eicosapentaenoic acid is present in an amount of 1%.

4. An ophthalmological composition according to claim 1, 2 or 3 in which the carrier comprises methyl cellulose.

5. An ophthalmological composition according to claim 4 in which the carrier solution is a 0.5% methyl cellulose solution.

6. An ophthalmological composition according to any of claims 1–5 in which the carrier comprises hydroxypropyl cellulose.

7. A method for the treatment of ocular inflammation, the method comprising topically administering eicosapentaenoic acid to the eye.

8. An ophthalmological composition comprising 0.5–1% by weight of eicosapentaenoic acid in a methyl cellulose, hydroxypropyl aqueous suspension.

* * * * *